United States Patent [19]

Singh et al.

[11] Patent Number: 4,973,747
[45] Date of Patent: Nov. 27, 1990

[54] PROCESS FOR PREPARING 3-HYDROXY 2-KETO ACIDS

[75] Inventors: Janak Singh, Lawrenceville; Richard H. Mueller, Ringoes, both of N.J.

[73] Assignee: E. R. Squibb & Sons, Inc., Princeton, N.J.

[21] Appl. No.: 394,369

[22] Filed: Aug. 15, 1989

[51] Int. Cl.⁵ .......................................... C07C 59/147
[52] U.S. Cl. .................................... 562/577; 562/464
[58] Field of Search ................................ 562/577, 464

[56] References Cited

U.S. PATENT DOCUMENTS 4,533,660  8/1985  Gordon et al. ...................... 514/210
4,638,061  1/1987  Slusarchyk et al. ................ 540/355
4,694,083  9/1987  Slusarchyk et al. ................ 546/14

OTHER PUBLICATIONS

M. T. Reetz et al., "A Mild and Variable Synthesis of -Keto-esters", Tetrahedron Letters, vol. 25, No. 5, pp. 511-514 (1984).
Radhakrishnan et al., *J. Biol. Chem.*, 235 (1960), 2322 to 2331.
Villeras et al., *Bull. Chem. Soc. Fr.*, (1970), 2699 to 2701.
Villeras et al., *C. R. Acad. Sc. Paris*, t. 267 (Nov. 25, 1968), 1502 to 1505, Series C.
Kirrmann et al., *Bull. Chem. Soc. Fr.*, (1968), 3213 to 3220.
Villeras et al., *Bull. Chem. Soc. Fr.*, (1970), 1450 to 1455.
Oh-hasi et al., *Bull. Chem. Soc. Jap.* 39 (1966), 2287 to 2289.

Primary Examiner—Paul J. Killos
Attorney, Agent, or Firm—Donald J. Barrack; Timothy J. Gaul

[57] ABSTRACT

A process has now been discovered by which an intermediate in preparation of antibiotics

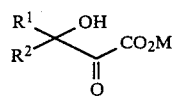

may be directly derived from the substrate

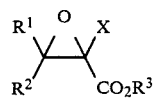

by treatment with aqueous solutions of $MHCO_3$ and $MOH$, wherein:

$R^1$, $R^2$ and $R^3$ are each independently alkyl, alkenyl, alkynyl, substituted alkyl, substituted alkenyl, substituted alkynyl, aryl, or substituted aryl;

M is alkali metal (such as Na, Li, or K); and

X is halogen.

16 Claims, No Drawings

PROCESS FOR PREPARING 3-HYDROXY 2-KETO ACIDS

Brief Description of the Invention

A process has now been discovered by which a product of the formula

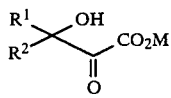   I may be directly derived from a substrate of the formula

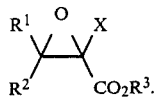   II

In the process of this invention, substrate II is treated first with an aqueous solution of IIIa

and then with an aqueous solution of IIb

to yield the product compound I. Compound I is an intermediate used to prepare antibiotics, particularly tigemonam.

In the formulas above and throughout this specification, the foregoing symbols are defined as follows:

$R^1$, $R^2$, and $R^3$ are each independently alkyl, alkenyl, alkynyl, substituted alkyl, substituted alkenyl, substituted alkynyl, aryl, or substituted aryl;

M is alkali metal (such as Na, Li, or K); and

X is halogen.

The process has the advantages of using inexpensive starting materials, avoiding handling of such hazardous substances as liquid bromine, and hydrolyzing the ester and halo epoxide groups in one step.

Detailed Description of the Invention

Listed below are definitions of various terms used to describe this invention. These definitions apply to the terms as they are used throughout the specification (unless they are otherwise limited in specific instances) either individually or as part of a larger group.

The terms "alkyl" and "alkoxy" refer to both straight and branched hydrocarbon groups. Those groups having 1 to 10 carbon atoms are preferred.

The term "alkenyl" refers to both straight and branched hydrocarbon groups having at least one double bond and may also contain one or more triple bonds. Those groups having 1 to 10 carbon atoms are preferred.

The term "alkynyl" refers to both straight and branched hydrocarbon groups having at least one triple bond and may also contain one or more double bonds. Those groups having 1 to 10 carbon atoms are preferred.

The term "aryl" refers to aromatic groups such as phenyl and naphthyl and includes polycyclic and heterocyclic aromatic groups such as furanyl and pyridyl.

The terms "halogen" and "halo" refer to chlorine, bromine and iodine.

The terms "substituted alkyl", "substituted alkenyl", and "substituted alkynyl" refer to those groups substituted with one or more of aryl, alkyl, alkenyl, alkynyl, hydroxy, alkoxy, halo, alkylthio, trimethylsilyl, dialkylamino, acylamino, alkoxycarbonylamino, carboxyl and aminocarbonylamino.

The term "substituted aryl" refers to aryl groups substituted with one or more of alkyl, alkenyl, alkynyl, hydroxy, alkoxy, halo, cyano, alkylthio, trimethylsilyl, dialkylamino, acylamino, alkoxycarbonylamino, carboxyl, protected carboxyl, and aminocarbonylamino.

The term "protected carboxyl" refers to a carboxyl group that has been esterified with a conventional ester protecting group. These groups are well known in the art; see, for example, U.S. Pat. No. 4,144,333, issued Mar. 13, 1979. The preferred protected carboxyl groups are benzyl, benzhydryl and t-butyl esters.

Compounds of formula II and preparation thereof are well known in the art. See, e.g., J. Villeras et al., Bull Soc. Chim. (1970), 1450; B. Castro et al., C. R. Series C, 267 (1968), 1502. Compound II may also be prepared following the procedures of the working examples included hereinafter.

Compound II as prepared in this manner may contain varying amounts of compound IIa

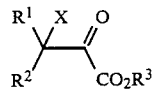   IIa as an impurity. Compound IIa also is converted to compound I on subsequent treatment as described below.

In the process of this invention, compound II may be treated with 1 Meq of an aqueous solution of compound IIIa, preferably a 0.5$\underline{N}$ solution of $NaHCO_3$. The mixture of compounds II and IIIa may be stirred for about 7 to 18 hours at about 0° to 30° C. A temperature of about 20° C. is preferred for this part of the process.

The above mixture may then be treated with 1 to 1.2 Meq of an aqueous solution of compound IIIb, preferably a 6 $\underline{N}$ solution of NaOH. The resulting mixture may be stirred for about 12 to 18 hours at a temperature of about 5° to 30° C. (20° C. perferred). Surprisingly, the treatment of compound II with compounds IIIa and IIIb causes hydrolysis of the ester and halo epoxide portions of compound II to yield compound I directly from compound II.

This solution of compound I may be used directly for the enzymatic reduction process described in U.S. patent application Ser. No. 316,353, filed Feb. 27, 1989. Alternatively, compound I may be isolated by adjustment to pH of about 6.4 (e.g., by addition of a dilute mineral acid such as HCl) followed by removal of water by evaporation or lyophilization.

Compound I, in turn, may be used in the preparation of the antibiotics disclosed in U.S. Pat. Nos. 4,533,660, 4,694,083, and 4,638,061, including tigemonam, [3S(Z)]-2-[[[1-(2-amino-4-thiazolyl)-2-[[2,2-dimethyl-4-oxo-1-(sulfooxy)-3-azetidinyl]amino]-2-oxoethylideneamino]oxy]acetic acid, the compound having the formula IV

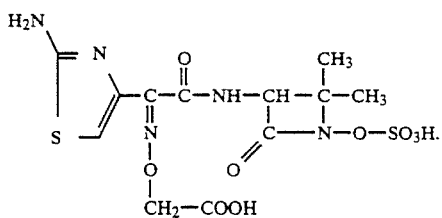

Using the procedure disclosed in U.S. patent application Ser. No. 316,353, filed Feb. 27, 1989, compound I may be treated with a nitrogen source (e.g., an ammonium salt) in the presence of an amino acid dehydrogenase, a transaminase, or microorganisms that produce such enzymes to yield a compound of the formula V

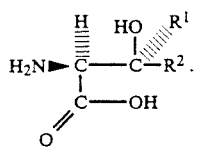

Leucine dehydrogenase is preferred for use in the reduction of Compound I to Compound V.

Compound V, in turn, may be treated with, e.g., di-tert-butyl dicarbonate in aqueous solution at a temperature of about 10° to 30° C and a pH of about 10 to 10.5 to yield a compound of the formula VI

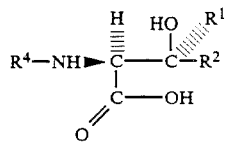

wherein $R^4$ is BOC (i.e.,

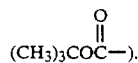

).

Alternatively, treatment with benzyloxy chloroformate in water/methyl isobutylketone at about 10°-30°, pH 9-10, (15°-20°, pH 9.5 preferred) to yield compound VI wherein $R^4$ is Z (i.e.,

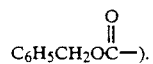

).

Compound VI ($R^4$=BOC) may be used to prepare tigemonam by the procedures disclosed in U.S. Pat. Nos. 4,638,061 and 4,694,083. Compound VI ($R^4$=Z) may also be used along similar lines.

The invention will now be further described by the following working example. All temperatures are in degrees Celsius unless otherwise indicated. The compound prepared in part A of the example will be referred to as "compound A" or "intermediate A" thereafter; likewise for the compounds prepared in parts B, C, D, etc. The working example shows preparation of a compound of formula II and the formation of a compound of formula I by the process of this invention. The working example is illustrative rather than limiting, so that the invention is limited only by the claims appended hereto.

Example 1

3-Hydroxy-3-methyl-2-oxobutanoic acid, monosodium salt

A. 2,2-Dichloroacetic acid, 1-methylethyl ester

A dry 3-necked flask (500 ml) was equipped with a stirring bar, thermocouple, and addition funnel, and connected through a drying tube to a Man gas trap. Isopropyl alcohol (IPA) (199 ml, 2.6 M) was added to the flask which was stirred in a water bath. $Cl_2CHCOCl$ (125 ml, 1.3M) was added via an addition funnel under $N_2$, keeping the temperature of the reaction mixture below 50°. After the addition of the acid chloride was complete, the mixture was stirred at 20° for 1 hour. Brine (250 ml), water (250 ml), and EtOAc (250 ml) were added and the layers were separated. The organic layer was washed with 5% $NaHCO_3$ (250 ml), and brine (100 ml). All aqueous layers were backwashed with ethyl acetate (100 ml). The organic layers were combined and dried ($MgSO_4$). The ethyl acetate was evaporated and the residue distilled through a vacuum-jacketed Vigreaux column at 1 atm to give ester compound A: boiling point 161°-168°, 193.12 g (yield 87%).

IR (neat): $\nu$ (C=O) 1738, 1760 cm$^{-1}$; $^1$HNMR (CDCl$_3$): $\delta$, 1.28 (d,6H,J=7 Hz), 5.1 (m,1H,J=7 Hz); 5.9 (s,1H) ppm.

Analysis calculated for $C_5H_8O_2Cl_2$: C,35.11; H,4.71; Cl,41.46.

Found: C,35.36; H,4.48; Cl,41.28.

B. 2-Chloro-3,3-dimethyloxiranecarboxylic acid, 1-methylethyl ester

Acetone (22.0 ml, 0.3M), compound A (42.8 ml, 0.3M), and toluene (100 ml, dried over 3 Å Molecular sieves, KF=0) were added to a 3-necked flask (500 ml) equipped with a magnetic stirrer, thermocouple, and addition funnel. The flask was chilled in an acetone/ice bath (−10°). K-t-amylate, [1.8M in toluene (titrated with HCl using phenolphthalein as indicator), 183 ml, 0.33M] was added to 25 ml dry toluene in the addition funnel. The K-t-amylate was added dropwise keeping the temperature of the reaction mixture <0° C. After the addition was complete (1 hour), the reaction mixture was stirred for 1 hour at 0° C., and quenched with brine (125 ml). The layers were separated, and the organic layer washed with 50% brine (125 ml×2), and brine (125 ml). All aqueous layers were backwashed with 100 ml toluene. The organic layers were combined and dried ($MgSO_4$). The toluene was evaporated. The residue was distilled through a 110 mm Vigreaux column giving 39.38 g (68%) of ester compound D, boiling point 45°-49°/1 mm.

IR (CHCl$_3$): $\nu$ (C=O) 1738 cm$^{-1}$, $^1$HNMR (CDCl$_3$): $\delta$, 1.27-1.34 (m,6H), 1.6 (s,3H); 1.8 (s,3H); 5.03-5.17 (m,1H) ppm, [for IIa ($R^3$=isopropyl), (~15%), 1.8 (s,6H), 5.1 (m,1H)] ppm; $^{13}$CNMR (CDCl$_3$): $\delta$, 19.7, 21.1, 21.2, 64.9, 70.5, 79.9, 163.8 ppm; [For II ($R^3$=isopropyl): $\delta$, 28.5, 68.3, 162, 192 ppm]; MS (CI): [M+NH$_4$]$^+$210.

Analysis calculated for $C_8H_{13}ClO_3$: C,49.78; H,6.81; Cl, 18.37.

Found: C,49.78; H,6.80; Cl,18.64.

C. 3-Hydroxy-3-methyl-2-oxobutanoic acid, monosodium salt

Chloroglycidic ester compound B (2.0 g, 10.4 mM) was added to a solution of NaHCO$_3$ (0.87 g, 10.4 mM)

in water (21 ml). The mixture was stirred for 7 hours, NaOH (6N, 2.1 ml, 12.6 mM) was added, and the mixture was stirred overnight. This solution may be used directly as described in U. S. patent application Ser. No. 316,353. Alternatively, the pH of the solution was adjusted to 6.4 with dilute hydrochloric acid. After lyophilization, the residue was dissolved in 10 ml H$_2$O and lyophilized again. The resulting white powder weighed 2.29 g (99%).

IR (KBr): (C=O) $\nu$ 1707, 1638, 1625 cm$^{-1}$, $^1$HNMR (CDCl$_3$): $\delta$, 1.48 (s,6H), 4.68 (—OH) ppm; MS (FAB): (M—H) 131; (M=2 Na—2H) 153.

Analysis calculated for C$_5$H$_7$O$_4$Na.1.16 NaCl.0.3 H$_2$O C,26.84; H,3.42; Cl,17.43; Na,21,57; H$_2$O, 2.42.

Found: C,27.15; H,3.56; Cl,17.99; Na,22.09; H$_2$O, 2.97 (KF).

What is claimed is:

1. A process for making a product of the formula

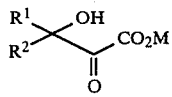

from a substrate of the formula

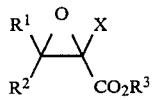

which comprises:
(a) treating the substrate with an aqueous solution of a first reactant of the formula MHCO$_3$; and
(b) treating the substrate with an aqueous solution of a second reactant of the formula MOH;

wherein:
R$^1$, R$^2$, and R$^3$ are each independently alkyl, alkenyl, alkynyl, substituted alkyl, substituted alkenyl, substituted alkynyl, aryl, or substituted aryl;
M is alkali metal; and
X is halogen.

2. The process of claim 1, wherein R$^1$ is alkyl.
3. The process of claim 1, wherein R$^1$ is methyl.
4. The process of claim 1, wherein R$^2$ is alkyl.
5. The process of claim 2, wherein R$^2$ is methyl.
6. The process of claim 1, wherein R$^3$ is alkyl.
7. The process of claim 1, wherein R$^3$ is —CH(CH$_3$)$_2$.
8. The process of claim 1, wherein M is sodium.
9. The process of claim 1, wherein X is chloro.
10. The process of claim 1 wherein R$_1$ and R$_2$ are methyl, R$_3$ is —CH(CH$_3$)$_2$ and M is sodium.
11. The process of claim 1, wherein the aqueous solution of the first reactant comprises about a 1 molar equivalent solution.
12. The process of claim 1, wherein the aqueous solution of the first reactant comprises about a 0.5$\underline{N}$ solution.
13. The process of claim 1, wherein the treatment with the first reactant is carried out at a temperature of about 0° to 30° C.
14. The process of claim 1, wherein the treatment with the first reactant is carried out at a temperature of about 20° C.
15. The process of claim 1, wherein the aqueous solution of the second reactant comprises about a 1 to 1.2 molar equivalent solution.
16. The process of claim 1, wherein the aqueous solution of the second reactant comprises about a 6$\underline{N}$ solution.

* * * * *